United States Patent [19]

Evans et al.

[11] Patent Number: 4,835,339
[45] Date of Patent: May 30, 1989

[54] TOMATO ANTHER CULTURE

[75] Inventors: David A. Evans, Palmyra; Robert A. Morrison, Cinnaminson, both of N.J.

[73] Assignee: Campbell Soup Company, Camden, N.J.

[21] Appl. No.: 829,511

[22] Filed: Feb. 14, 1986

[51] Int. Cl.$^4$ .......... A01H 1/04; A01H 1/00; C12N 5/00
[52] U.S. Cl. .......... 800/1; 47/58; 47/DIG. 1; 435/240.45; 435/240.51; 435/240.54
[58] Field of Search .......... 435/240.4, 240.45, 240.51, 435/240.54; 47/58, DIG. 1; 800/1

[56] References Cited

U.S. PATENT DOCUMENTS 4,241,536 12/1980 Saint-Fermn .......... 47/58

OTHER PUBLICATIONS

P. M. Greishoff et al., (1972), Planta 107, 161–170.
G. B. Collins (1977), Crop Science, 17, 583–586.
J. Tanick (1972), Horticultural Science, W. H. Freeman & Co., San Francisco, CA, 381.
C. C. Chee (1982), Haploids in Plant Development in Plant Improvement and Sanatic Cell Genetics I & Vasil, eds Academic Press Inc., NY.
C. Nitsil et al. (1982), in Variability in Plants Regenerated from Tissue Culture, E. D. Earle et al. eds, Praegen Publishers, NY, 69–91.
Ancora et al. (1977), Z. Pflanzenphyscol. Bd., 82 S, 377–88.
Sibi et al. (1979), Ann. Amelcir. Plants, 29:583–606.
Cappadocia et al. (1980), Plant Sci. Lett., 20:157–166.
Zamir et al. (1980), Plant Sci. Lett., 17:353–61.
Zamir et al. (1981), Plant Sci. Lett., 21:223–27.
Gulshan et al. (1981), Biologia Plant, 23:414–20.
Zagorska et al. (1982), Comptes Redus de L'Acad. Bulg. des Sciences, 35:97–100.
Debergh et al. (1973), C. R. Acad. Sci. Paris, Serier D, 176:1281–4.
Ramulu et al. (1976), S. Pflanzenzucht, 76:298–319.
Collins (1976), Crop Sci., 17:583–86.
Levenko et al. (1977), Phytomorphology, 27:377–383.
Sharp et al. (1971), Bull. Torrey Bot. Club, 98:219–222.
Gresshoff et al. (1972), Planta, 107:161–170.
Sharp et al. (1972), Planta, 104:357–361.
Nitsch et al. (1969), Science, 163:85–87.

Primary Examiner—Alvin E. Tanenholtz
Assistant Examiner—Charles E. Cohen
Attorney, Agent, or Firm—Banner, Birch, McKie & Beckett

[57] ABSTRACT

A method is disclosed for forming haploid tomato plants. Plants so formed are normal, flowering plants but are sterile. Methods are taught of doubling the chromosome number of the haploid plants to form fetile, true breeding diploid tomato plants. Such methods are useful in plant breeding programs to produce new assortments of genes in true-breeding lines without the several backcrossing steps otherwise required.

16 Claims, 1 Drawing Sheet

GOT
LE Hy An LP

PGM
LE Hy Anth LP

PGI
LE Hy Anth LP

PER
LE Hy An LP

TOMATO ANTHER CULTURE

FIELD OF THE INVENTION

The present invention relates to the field of breeding new genetic varieties of vegetables and in particular, methods for use in tomato breeding.

BACKGROUND OF THE INVENTION

Haploid organisms contain the same number of chromosomes (n) in their somatic cells as do the normal gametes of the species. The ploidy level of a somatic cell is defined as the number of sets of the haploid number of chromosomes that the cell contains. For example, humans are diploid organisms, having 2 n chromosomes in somatic cells. When the ploidy level is greater than one, it is often difficult to know which genes the organism possesses, due to dominance. When more than one copy of a gene is present only one copy may be expressed, the dominant one. The other copy of the gene, the recessive allele, is said to be masked because its presence is not apparent at the phenotypic level.

The existence of haploid organisms can simplify the process of plant breeding. Due to the absence of dominance effects in haploids, the phenotype is an accurate representation of the genotype. For these and other reasons, which will be apparent to those skilled in the art, the availability of haploids in a particular species can be a powerful tool in a plant breeding program.

Spontaneous haploids occur in many species, albeit at low frequencies. Haploid plants of certain species have also been recovered by various laboratory manipulations, including parthenogenesis, androgenesis, chromosome elimination, and tissue culture methods. However, with few exceptions, the yield of haploids obtained with these techniques is not great enough to be practical for use in a breeding program. Furthermore, the actual technique used, seems to vary from species to species such that a successful protocol for generating haploids in carrot, for example, will not necessarily be successful for pepper.

SUMMARY OF THE INVENTION

It is an object of the present invention to provide a method for producing haploid tomato plants.

It is another object of the invention to provide a haploid tomato plant which is capable of forming flowers.

It is an object of the present invention to provide a method of producing a true breeding, diploid tomato plant.

In accordance with these objects, a method is provided for producing haploid tomato callus tissue or embryos comprising:

providing an inflorescence from a diploid tomato plant;

incubating said inflorescence at about 3°–5° C. for about 2 to about 6 days;

excising the anthers of said inflorescence, said anthers containing microspores at the late uninucleate stage;

culturing said anthers at about 34°–38° C. for about 7 to about 9 days in the dark, on a medium comprising from about 7–12% sucrose, about $5 \times 10^{-8}$ to about $5 \times 10^{-9}$M of a plant hormone which stimulates both plant cell division and elongation, and about $5 \times 10^{-8}$ to about $5 \times 10^{\times 9}$M of a plant hormone which stimulates plant cell division;

transferring said cultured anthers to a temperature of about 22°–30° C. with a 12–18 hour light period for about 3 to 5 days;

transferring said cultured anthers to a medium comprising about 3 to 6% sucrose, and about $5 \times 10^{-7}$ to $5 \times 10^{-8}$M of a plant hormone which stimulates cell division, for about 6–10 weeks to form haploid callus tissue or embryos.

The callus tissue or embryos formed are subsequently cultured on hormone containing media to produce a haploid plant. Embryos so formed alternatively may be cultured directly on hormone-free medium to produce a haploid plant. Also provided by the present invention are the haploid tomato plants produced by the above method which produce flowers, and methods for producing true breeding, diploid tomato plants from said haploid tomato plants.

Applicants have found a method which is reproducible for generating haploid tomato plants. The haploids are normal plants, that is, they have regular leaves, stems and roots, and produce flowers. As expected, these plants are sterile, producing neither seed nor fruit. However, when the chromosome number of the haploids is doubled, fertile, homozygous diploids result which set fruit and seed. Use of such completely homozygous, pure lines, circumvents the six to seven generations of backcrossing otherwise necessary to stabilize a line of tomato plant.

BRIED DESCRIPTION OF THE FIGURES

FIG. 1, panels a–d, show zymograms for four different enzymes, comparing a haploid plant, its diploid hybrid parent, and the wild plants which were crossed to form the hybrid.

(a) glutamate oxaloacetate transaminase (GOT)
(b) phosphoglucomutase (PGM)
(c) phosphoglucoisomerase (PGI)
(d) peroxidase (PER).

DETAILED DESCRIPTION OF THE INVENTION

Figure 1A:
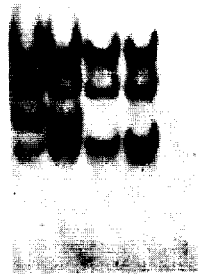

The present invention may be practiced using any of the species related to a cultivated tomato. These include *Lycopersicon peruvianum, L. pennellii, L. pimpinellifolium, L. cheesmanii, L. esculentum, L. hirsutum, L. chilense, L. glandifolium, L. chmielewskii, L. parviflorum*, and *Solanum lycopersicoides*. In addition, the use of interspecific hybrids is contemplated in order to obtain new assortments of genes. Particularly useful strains of tomato used in the practice of the invention have been obtained from Charles Rick, University of California at Davis (*L. esculentum* IMS007 and *S. lycopersicoides* LA 1964), and the Goldsmith Seed Co., Gilroy, Calif. (GS27 hybrid).

In the practice of the method of the present invention, it is important to use anthers of the proper developmental stage; optimal response has been found when anthers contain uninucleate microspores. Preferably, these microspores are just prior to the first pollen mitosis. To determine the stage of development, a large number of anthers are analyzed cytologically, using a carmine-based stain. Applicants have found that it can be misleading to try to rely on an assumed correlation between flower bud morphology and anther development. Any such correlation can be affected by genotype and growth conditions of the plants.

It is preferred that the anthers are taken from inflorescences of young, healthy plants. There may be seasonal differences among greenhouse plants as to the response of the anthers. Inflorescences are incubated at about 3°-5° C. for 2-6 days. Such a cold shock treatment is thought to result in an increased number of callus tissue or embryos per anther.

Media which can be used for culturing the anthers to produce callus tissue or embryos contain relatively high amounts of potassium, nitrogen and phosphorous salts as macronutrients, high levels of micronutrients as well as vitamins and amino acids, such as CM medium of Sibi et al. (Ann. Amerlior. Plant, volume 29, pp. 583–606, 1979.) The media are supplemented with 7-12% sucrose, preferably about 10%. Levels of plant hormones which stimulate both cell division and cell elongation, such as (2,4-dichlorophenoxy)-acetic acid, and of plant hormones which stimulate cell division (e.g., cytokinins, such as kinetin,) are between about $5 \times 10^{-8}$ and $5 \times 10^{-9}$M. The media may be solidified, for example, with about 1% agarose.

During the first about 7-9 days of incubation, the anther cultures should be kept in the dark, at above-ambient temperature conditions, preferably about 34°-38° C. A light regime should be initiated thereafter of about 12-18 hours per day and the incubation temperature should be lowered to about 22°-30° C. This regime should continue for about 3-5 days.

The anther cultures should then be transferred to a secondary medium, substantially the same as the initiation medium, however, containing a lower concentration of sucrose, (about 3-6%), and about tenfold higher concentrations of plant hormones which stimulate cell division (about $5 \times 10^{-7}$ to $5 \times 10^{-8}$M). The secondary medium need contain no auxin-type hormones (which stimulate cell elongation), however, low levels, such as about $10^{-7}$ to $10^{-8}$M is thought to improve the frequency of callus or embryo formation. The secondary medium may be solidified, like the initiation medium, with agarose.

Embryos which form on the secondary medium may be cultured directly on hormone-free medium. Alternatively, the embryos may be treated like the callus, as described below. To determine whether the cultured anthers have formed callus tissue or embryos, visual inspection should be performed. Callus tissue has an irregular shape whereas embryos are spherical. At late stages the embryos have rudimentary plant organs, such as cotyledons and radicals. These are observable by the naked eye, or assisted by a magnifying glass, as is well known to those skilled in the art.

Any callus or embryo which has formed on the secondary medium may be isolated away from the remaining anther tissue and cultured on any suitable culture medium, such as for example, Murashige and Skoog (MS) (Physiol. Plant. Volume 15, pp. 473–497 1962). Such medium contains high levels of patassium, nitrogen and phosphorous salts as macronutrients, as well as relatively high levels of micronutrients. To stimulate shoot formation from the undifferentiated callus tissue or embryos, a plant hormone which stimulates cell division such as 6-benzylaminopurine or zeatin riboside may be added at concentrations of from about $10^{-5}$ to $10^{-6}$M, as is well known in the art. To allow for root formation, the callus-cum-shoot or embryos may be transferred to a culture medium containing 0 to about 1 $\mu$M of a plant hormone which stimulates cell division. Once shoots and roots have developed, the plantlet may then be planted in any suitable medium for plant growth, such as soil, vermiculite, and the like.

It is preferred that the haploid nature of the plantlets be verified prior to using for making diploids. The direct means of determining ploidy level is by cytological analysis. Actively growing root tips or callus tissue may be used for determining chromosome method. In one method, a modification of the Burn's technique (Tobacco Science, 158: 1-2 (1964)), cells are pretreated for 3-4 hours in a solution of 8-hydroxyquinoline and maltose under constant aeration, squashed, and stained with aceto-orcein for one minute (Darlington and LeCour, 1962, *The Handling of Chromosomes*, Hafner Publishing Co., New York).

Chromosome doubling of haploid tomato plants may be achieved by any of the techniques known in the art for other plants. Many of these methods were developed to obtain polyploids from diploids. Tissue-wounding, and subsequent callus formation is one of the earliest techniques used to double chromosome number. Callus formation is usually induced by decapitation of the shoot tip and removal of all axillary buds. Shoots that develop from the callus frequently have an increased ploidy level.

Colchicine, an alkaloid extract of the autumn-flowering crocus, can be used to double the chromosome number of haploids. It can be applied as an aqueous solution, but it can also be dissolved in a weak alcohol or 10% glycerine with water, or applied as a lanolin or agar paste. Applicants have found that concentrations of about 0.1 to 1% colchicine are suitable for doubling the chromosomes of haploid tomato plants. The colchicine may be applied at the axils of the leaves of the tomato plants, or alternatively, the roots of the young tomato plans may be immersed in the colchicine solution for 24-28 hours, after which the roots are washed thoroughly and replanted in medium lacking colchicine.

Leaves of haploid tomato plants may be cultured in vitro on medium supplemented with from about 1 to 10 $\mu$M 6-benzylaminopurine to form callus from cells which have spontaneously become diploid via endomitosis. Endomitosis is a natural phenomenon which occurs in certain plant tissues wherein the spindle apparatus does not form and the metaphase plate is eliminated. Thus, nuclei are formed having twice the number of chromosomes. The callus may be subsequently removed from this media so that plants are formed. Plants can be selected from among those formed which set fruit and seed, indicating that they have diploidized.

EXAMPLE 1

This example demonstrates the hemizygous nature of the haploid plants derived by the method of the present invention and shows that new assortments of genes are obtained.

Haploid plants (n=12) were produced by the method of the present invention. The anthers used to form embryos were derived from an $F_1$ hybrid plant of, *L. esculentum* $\times$ *L. pennellii*. The $F_1$ hybrid was diploid (2n=24), as were each of its wild parents.

Figure 1B:
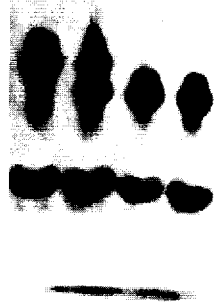
Figure 1C:
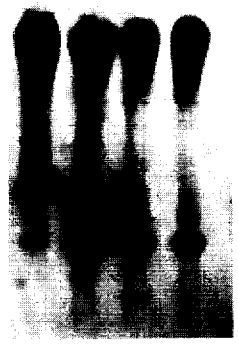
Figure 1D:
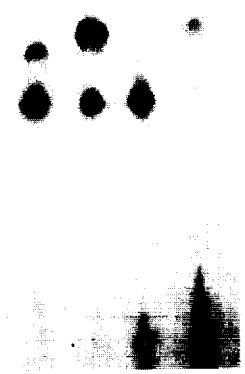

Zymograms were run of tissue derived from the anther-derived, haploid plant. Adjacent lanes of the zymograms contained tissue of each of the wild parents and of the $F_1$ hybrid. Results can be seen in the FIG. 1, panels a-d. Zymograms were performed by electrophoresis of the enzyme preparations in starch gels, as described by Tanksley (1979) Tomato Gen. Coop. Report No. 29: 37-38. Histochemical stains used for detection of the enzymes are as published: (1) glutamate oxaloacetate transaminase as in Plant Syst. Evol. 127, 139-170 (1977); (2) phosphoglucomutase as in Biochemical Genetics 17, 1159-1164 (1979); (3) phosphoglucoisomerase as in Canadian J. Genet. Cytol. 22, 271-278 (1980); (4) peroxidase as in Plant Syst. Evol. 127, 139-170 (1977).

In panel (a), the gel was stained for the enzyme glutamate oxaloacetate transaminase (GOT). The two wild parental lines had different banding patterns from each other. The $F_1$, hybrid line displayed all bands of both parents (i.e., was heterozygous for GOT.) In contrast, the haploid, anther-derived plant had only the bands of the L. pennellii parent, suggesting hemizygosis. Similar results are shown in panels (b) and (c), which were stained for the enzymes phosphoglucomutase (PGM) and phosphoglucoisomerase (PGI).

When the gels were stained for the enzyme peroxidase (PER), a different result was obtained. The anther-derived haploid again appeared hemizygous, but it displayed the PER banding pattern of the L. esculentum parental line.

EXAMPLE 2

This example demonstrates the utility of the present invention in providing plant lines having new assortments of genes.

Two regenerates of anther callus derived from hybrids of IMS007 (x) LA 1964 of the species *L. esculentum* and *Solanum lycopersicoides* were analyzed for three characteristics: leaf morphology, leaf-trichome covering, and internode length. The following results were obtained.

Several regenerates had a leaf morphology characterized by expanded leaf margins. Since the margins of LA 1964 (*S. lycopersicoides*) were narrow, this observation suggests introgression of genes from the IMS 007 (*L. esculentum*) parent. Thick trichome covering of the leaves was also observed among several of the regenerates, a trait characteristic of the IMS 007 parent. Long internode length, a trait characteristic of the LA 1964 parent, was also observed among the regenerates. Thus, traits characteristic of both parents were found among the haploid regenerates of anther callus derived from hybrid plants.

Further, a regenerate of an embryo derived from a hybrid of *L. esculentum* (x) *L. pennellii* was analyzed for (a) leaf morphology, (b) branching pattern, and (c) leaf volatiles. The first two characteristics were similar to the *L. pennellii* parent, whereas the last character was similar to the *L. esculentum* parent. Thus, although the regenerate had only N=12 chromosomes, individual characteristics came from each parental donor.

The present invention is not limited by the examples employed, but is defined by the claims appended below.

We claim:

1. A method of producing a haploid tomato plant comprising:
   providing an inflorescence from a diploid tomato plant;
   incubating said inflorescence at about 3°-5° C. for about 2-6 days;
   excising the anthers of said inflorescence, said anthers containing microspores at the late uninucleate stage;
   culturing said anthers at about 34°-38° C. for about 7 to about 9 days in the dark, on a suitable medium comprising from about 7-12% sucrose, about $5\times10^{-8}$ to $5\times10^{-9}$M of a hormone which stimulates both plant cell division and elongation, and about $5\times10^{-8}$ to $5\times10^{-9}$M of a hormone which stimulates plant cell division;
   transferring said cultured anthers to an environment having a temperature of about 22°-30° C. with a 12-18 hour per day light period for about 3 to 5 days;
   reculturing said cultured anthers on a suitable medium comprising about 3 to 6% sucrose, and about $5\times10^{-7}$ to $5\times10^{-8}$M of a hormone which stimulates plant cell division for about 6 to about 10 weeks;
   visually inspecting the cultured anthers to identify embryos;
   transferring said embryos to a suitable hormone-free, growth medium to form a haploid plant.

2. A method of producing a haploid tomato plant comprising:
   providing an inflorescence from a diploid tomato plant;
   incubating said inflorescence at about 3°-5° C. for about 2-6 days;
   excising the anthers of said inflorescence, said anthers containing microspores at the late uninucleate stage;
   culturing said anthers at about 34°-38° C. for about 7 to about 9 days in the dark, on a suitable medium comprising from about 7-12% sucrose, about $5\times10^{-8}$ to $5\times10^{-9}$M of a hormone which stimulates both plant cell division and elongation, and about $5\times10^{-8}$ to $5\times10^{-9}$M of a hormone which stimulates plant cell division;
   transferring said cultured anthers to an environment having a temperature of about 22°-30° C. with a 12-18 hour per day light period for about 3 to 5 days;
   reculturing said cultured anthers on a suitable medium comprising about 3 to 6% sucrose, and about $5\times10^{-7}$ to $5\times10^{-8}$M of a hormone which stimulates plant cell division for about 6 to about 10 weeks to form callus tissue or embryo;
   isolating said callus tissue or embryo from remaining anther tissue and transferring it to a shooting medium supplemented with about 1 to about 10 μM of a hormone which stimulates plant cell division, to stimulate shoot growth; and
   transferring said shoot or embryo to a culture medium supplemented with from 0 to about 1 μM of a hormone which stimulates plant cell division, to stimulate root growth, forming a haploid plant.

3. The method of claim 1 wherein the plant hormone which stimulates cell division is selected from the group consisting of 6-benzylaminopurine, zeatin riboside, and kinetin.

4. The method of claim 1 wherein the plant hormone which stimulates both cell division and cell elongation is (2,4-dichlorophenoxy)-acetic acid.

5. The method of claim 1 wherein the anthers are dissected from an inflorescence of a hybrid plant of *L. esculentum* (X) *L. pennellii*.

6. The method of claim 2 wherein the plant hormone which stimulates cell division is selected from the group consisting of 6-benzylaminopurine, zeatin riboside, and kinetin.

7. The method of claim 2 wherein the plant hormone which stimulates both cell division and cell elongation is (2,4-dichlorophenoxy)-acetic acid.

8. The method of claim 2 wherein the anthers are dissected from an inflorescence of a hybrid plant of *L. esculentum* (×) *L. pennellii*.

9. A flowering haploid tomato plant which is derived from anther tissue.

10. A method of producing a true breeding, diploid tomato plant comprising:
  forming a haploid plant according to the method of claim 1; and
  applying 0.1 to 1% colchicine to said haploid tomato plant at the axils of the leaves of said haploid tomato plant, and selecting plants which set fruit and seed.

11. A method of producing a true breeding, diploid tomato plant comprising:
  forming a haploid tomato plant according to the method of claim 1; and
  treating said haploid tomato plant with about 0.1 to 1% colchicine for 24 to 48 hours, washing thoroughly, replanting in a suitable growth medium and selecting plants which set fruit and seed.

12. A method of producing a true breeding, diploid tomato plant comprising:
  forming a haploid tomato plant according to the method of claim 1; and
  culturing, in vitro, the leaves of said haploid tomato plant on medium supplemented with about 1 to 10 $\mu$M of a plant hormone which stimulates cell division to regenerate plantlets from cells which have become diploid, removing the plantlets to a suitable growth medium to form plants, and selecting those plants which set fruit and seed.

13. A method of producing a true breeding, diploid tomato plant comprising:
  forming a haploid tomato plant according to the method of claim 1; and
  continuously cutting back said haploid plant until a fruit- and seed-setting plant results.

14. A haploid tomato plant of claim 9 derived from the anther tissue of an *L. esculentum* (×) *L. pennellii* interspecific hybrid.

15. A haploid tomato plant of claim 9 derived from the anther tissue of an *L. esculentum* (×) *S. lycopersicoides* interspecific hybrid.

16. A haploid tomato plant of claim 9 derived from anther tissue of a GS27 hybrid.

* * * * *